United States Patent [19]
Lyons

[11] Patent Number: 5,635,536
[45] Date of Patent: Jun. 3, 1997

[54] EMULSION SUITABLE FOR ADMINISTERING A SPHINGOLIPID

[75] Inventor: Robert T. Lyons, Cary, N.C.

[73] Assignees: Pharmacia & Upjohn Aktiebolag, Stockholm, Sweden; Eli Lilly and Company, Indianapolis, Ind.

[21] Appl. No.: 351,635

[22] Filed: Dec. 7, 1994

[51] Int. Cl.$^6$ .................................................. A61K 31/20
[52] U.S. Cl. ........................... 514/558; 514/560; 514/937
[58] Field of Search ..................................... 514/558, 560, 514/937

[56] References Cited

U.S. PATENT DOCUMENTS

| | | | |
|---|---|---|---|
| H1168 | 4/1993 | McKenna et al. | 514/28 |
| Re. 32,393 | 4/1987 | Wretlind et al. | 514/219 |
| 4,280,996 | 7/1981 | Okamoto et al. | 424/199 |
| 4,757,053 | 7/1988 | della Valle et al. | 514/42 |
| 4,816,450 | 3/1989 | Beil et al. | 514/25 |
| 4,897,381 | 1/1990 | della Valle et al. | 514/25 |
| 4,937,232 | 6/1990 | Bell et al. | 514/26 |
| 5,149,794 | 9/1992 | Yatvin et al. | 536/29 |
| 5,149,860 | 9/1992 | Zysman et al. | 560/160 |
| 5,198,470 | 3/1993 | Zysman et al. | 514/785 |
| 5,364,632 | 11/1994 | Benita et al. | 424/450 |

FOREIGN PATENT DOCUMENTS

| | | |
|---|---|---|
| 0391369A2 | 10/1990 | European Pat. Off. . |
| 0391369B1 | 8/1994 | European Pat. Off. . |
| 0456106B1 | 12/1994 | European Pat. Off. . |

OTHER PUBLICATIONS

CA 119:278770, Benita et al., 1993.

Remington's Pharmaceutical Sciences, 18$^{th}$ Ed., 1990, pp. 300–303.

Scaro et al., Experientia, vol. 38, No. 3, 1982, pp. 401–403.

Srivastava et al., Liquid Membrane Phenomena and Drug Action, Advances in Colloid and Interface Science, vol. 20 (1984), pp. 131–161.

Burke, Sphingosomes in Skincase, Manufacturing Chemist, Jul., 1990, pp. 36–37.

Imokawa et al., Importance of intercellular lipids in water-retention properties of the stratum corneum: induction and recovery study of surfactant dry skin, Arch. Dermatol. Res. (1989), vol. 281, pp. 45–51.

Sweeley, Sphingolipids, Chapter 11, D.E. Vance and J. Vance (Eds.) Biochemistry of Lipids, Lipoproteins and Membranes, 1991, pp. 327–361.

Hannun et al., Sphingolipid breakdown products: anti-proliferative and tumor-suppressor lipids, Biochimica et Biophysica Acta., vol. 1154, 1993, pp. 223–236.

Franson et al., Sphingolipid metabolism and signal transduction: inhibition of in vitro phospholipase activity by sphingosine, Biochimica et Biophysica Acta., vol. 1136, 1992, pp. 169–174.

Hannun et al., Regulation of protein kinase C by sphingosine and lysosphingolipids, Clinica Chimica Acta., vol. 185, 1989, pp. 333–346.

Merrill, Jr., et al., Modulation of protein kinase C and diverse cell functions by sphingosine—a pharmacologically interesting compound linking sphingolipids and signal transduction, Biochimica et Biophysica Acta., vol. 1010, 1989, pp. 131–139.

Michell et al., Sphingolipid signalling, Second Messengers, Current Biology, vol. 4, No. 4, 1994, pp. 370–374.

Becher, Emulsions: Theory and Practice, Second Edition, American Chemical Society, Monograph Series, Robert E. Krieger Publishing Company, New York, 1977, pp. 1–2; 118–132.

Emulsions in Pharmacy, Remington's Pharmaceutical Sciences, Chapter 19, 18th Edition, 1990, pp. 298–309.

Becher, Encyclopedia of Emulsion Technology, vol. 1, Basic Theory, Marcel Dekker, Inc., New York, pp. 152–159 (1983).

McFadyen, Electrophoretic mobility and zeta potential of colloidal particles, American Laboratory, Apr., 1987, pp. 64–75.

Lehninger, The Molecular Basis of Cell Structure and Function, Biochemistry, Second Edition, Chapter 11, Lipids, lipoproteins, and membranes, Worth Publishers, Inc., pp. 291–292 (1975).

*Primary Examiner*—Kimberly Jordan
*Attorney, Agent, or Firm*—Pollock, Vande Sande & Priddy

[57] ABSTRACT

An acid emulsion comprising a lipoid dispersed in an aqueous phase, a cationic sphingolipid, and a stabilizing amount of non-ionic surfactant and cholesterol is provided, along with the method of administering the emulsion.

17 Claims, 1 Drawing Sheet

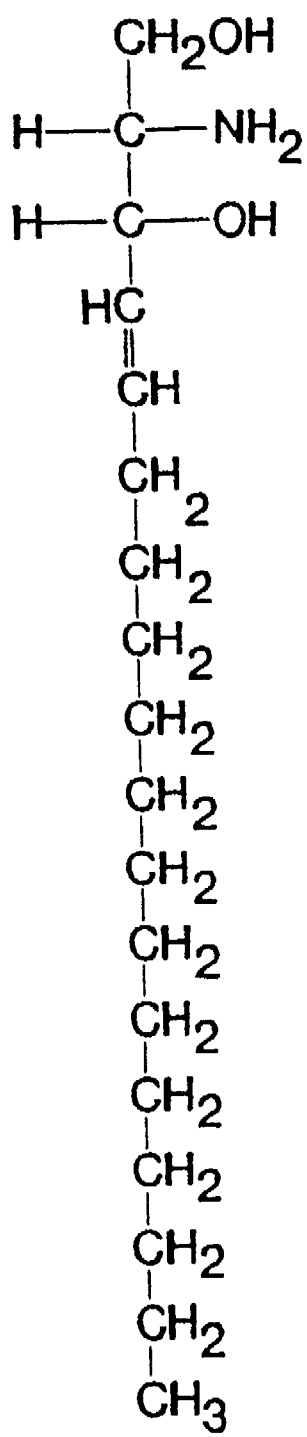
SPHINGOSINE
(4-SPHINGENINE)
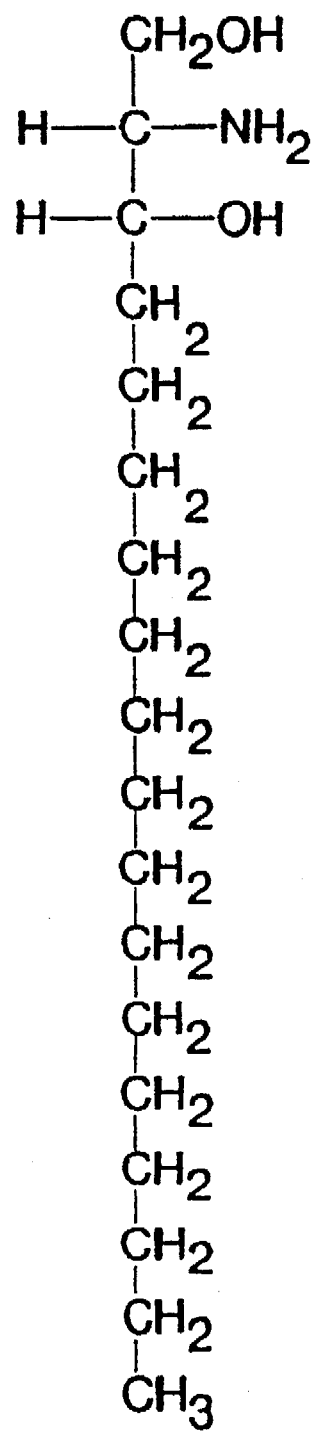
DIHYDROSPHINGOSINE
(SPHINGANINE)

EMULSION SUITABLE FOR ADMINISTERING A SPHINGOLIPID

TECHNICAL FIELD

The present invention is concerned with a delivery system for administering a sphingolipid and especially concerned with a stable oil-in-water emulsion containing the sphingolipid. The present invention is also concerned with methods of administering the emulsion to a patient in need thereof including oral and intravenous administration.

BACKGROUND OF THE INVENTION

Sphingolipids are complex lipids containing as their backbone sphingosine or a related base. These important membrane components in both plant and animal cells are now believed to perform critical regulatory roles in cell growth and differentiation. Functioning as "lipid second messengers," these molecules are part of a cascade of biochemical events which transmit signals from a broad array of circulating external stimuli, eventually triggering events within the cell nucleus. These external stimuli, considered "first messengers," include growth factors, hormones, and neurotransmitters. This signal transduction cascade also involves modulating the activity of certain key intracellular enzymes. Protein kinase C (PKC) is an example of a group of such regulatory enzymes.

PKC has evolved as a major target for therapeutic intervention in diseases involving disordered cell growth and inflammation. Certain sphingolipid derivatives are now known to be potent inhibitors of PKC activity and are therefore considered to be candidates for novel therapeutic agents. One major clinical application now being evaluated is overcoming multi-drug resistance in certain cancers by inhibiting ("down-regulating") an intracellular, PKC-modulated "drug pump." During development and testing of certain sphingolipids for use as potential drugs, the need arose for a pharmaceutically acceptable vehicle to allow for a safe intravenous administration into animals and eventually into humans. Sphingolipids contain a molecule of sphingosine or one of its derivatives or isomers. One end of the sphingolipid, referred to as the tail, possesses a lipophilic, long-chain fatty acid. The other end, referred to as the head, is a hydrophilic group (see FIG. 1). Sphingosine, possessing a primary amine group, is cationic (basic) at physiological pH ($pK_a$ ~6.5). With a non-polar lipophilic tail and a polar hydrophilic head, this molecule is considered to be amphiphilic and surface-active since it tends to orient at the interface between oil and water phases.

Sphingolipids are poorly water-soluble and tend to form large aggregates when placed in an aqueous environment by themselves. Therefore, it is desirable to be able to employ sphingolipids in a lipid-based delivery system such as an oil-in-water emulsion. However, attempts by the inventor of the present application to incorporate sphingolipids into conventional soybean oil emulsions, stabilized by mixed phospholipids purified from egg yolk, were unsuccessful. This is quite unfortunate since phospholipids purified from soybeans or egg yolk are the stabilizers of choice for oil-in-water emulsions intended for intravenous administration, including those to be used for parenteral nutrition as well as for those designed lipid-based drug delivery. Typically, the dispersed oil droplets in these emulsions are stabilized by layers of associated water molecules as well as by a net negative surface charge. In fact, the major component in phospholipid mixtures, phosphatidyl choline, is zwitterionic in form and neutral over a wide pH range. Therefore, this surface charge, also known as the Zeta potential, actually derives from small amounts of naturally occurring ionized lipids in the phospholipid mixture as well as from trace levels of free fatty acids which are hydrolyzed from the emulsifier and/or the oil phase during processing and sterilization at elevated temperatures.

Phospholipid-stabilized fat emulsions of the type described above are well-suited for parenteral nutrition or for the intravenous delivery of non-ionic lipophilic drugs. Well-known examples of the former include Intralipid® and Liposyn®. Good examples of the latter include Dizac™, which contains the sedative diazepam, and Diprivan™, which delivers the anesthetic propofol. In cases where the pharmacological agent contains an anionic functional group at physiological pH, emulsion droplet Zeta potential may become even more electronegative, often resulting in enhanced physical stability. However, applicant tried unsuccessfully many times to produce a phospholipid-stabilized fat emulsion containing a sphingolipid.

SUMMARY OF INVENTION

It is therefore an object of the present invention to provide a stable, lipid-based formulation capable of delivering a cationic sphingolipid. It has been found pursuant to the present invention that an oil-in-water emulsion containing cholesterol and having a pH of about 2 to about 6 provides a stable, lipid-based formulation capable of delivering cationic sphingolipids to a patient.

More particularly, the present invention is concerned with an emulsion for administering a cationic sphingolipid to a patient in need thereof, which comprises a pharmacologically acceptable lipid as a hydrophobic phase dispersed in a hydrophilic phase, an effective amount of the cationic sphingolipid, and cholesterol in an amount sufficient to stabilize the emulsion. The emulsion has a pH of about 2 to about 6.

The present invention is also concerned with treating a patient by administering the above described emulsion to a patient in need thereof.

SUMMARY OF DRAWINGS

FIG. 1 shows the structural formula for sphingosine and dihydrosphingosine.

BEST AND VARIOUS MODES FOR CARRYING OUT INVENTION

The sphingolipids employed in the present invention are the sphingosine bases and include sphingosine [4-sphingenine], dihydrosphingosine [sphinganine], the isomers D, L, or DL-threo-dihydrosphingosine, lysosphingolipids, and the pharmaceutically acceptable acid salts thereof.

The hydrophobic component comprises a pharmaceutically acceptable triglyceride such as an oil or fat of a vegetable or animal nature and preferably is chosen from the group consisting of soybean oil, safflower oil, marine oil, sunflower seed oil, corn oil, black currant seed oil, borage oil, palm kernel oil, cotton seed oil, olive oil, or coconut oil distillates (medium chain triglycerides, typically $C_8$–$C_{10}$). Mixtures of oils can be employed, if desired.

The emulsions of the present invention usually have a fat or oil content of about 5 to about 50 (w/v) %, preferably about 10 to about 30 g/100 ml, a typical example being about 20 g/100 ml of the emulsion.

In addition, the emulsion should exhibit a pH of about 2 to about 6 and preferably about 4. The pH can be adjusted to the desired value, if necessary, by adding a pharmaceutically acceptable acid such as hydrochloric acid, phosphoric acid, or sulfuric acid.

The emulsion also includes water in the necessary amount to provide the desired volume.

If desired, the emulsion can include auxiliary ingredients such as nonionic surfactants, tonicity-adjusting agents, antioxidants, nutritive agents, trace elements, and vitamins. The emulsion is preferably at least substantially, if not entirely, free of phospholipids of animal or vegetable origin.

When an auxiliary nonionic surfactant is present, such is typically used in amounts of about 0.10 to about 5 grams/100 ml, preferably about 0.5 to about 2 grams/100 ml, an example of which is about 1 gram/100 ml.

Preferred non-ionic surfactants are the block copolymers of polyoxypropylene and polyoxyethylene that are also known as poloxamers. These are available under the trade designation Pluronics (BASF Corporation, Parsippany, N.J.). These surfactants tend to prolong the circulation time of the emulsion droplets in plasma.

Other examples of non-ionic surfactants include those classified as polyoxyethylene fatty acid esters. In this group, sorbitan monooleate polyoxyethylene, also known as polysorbate 80 or Tween 80 (ICI Americas, Wilmington, Del.) is most useful.

The isotonic agents when employed are typically used in amounts of about 0.8 to about 8 g/100 ml, preferably about 1 to about 3 grams/100 ml, an example of which being 2 gram/100 ml. These materials regulate the osmotic pressure to make the emulsion isotonic with the blood.

Examples of some isotonic agents are glycerin and certain sugar alcohols, such as xylitol, sorbitol, and mannitol. Other examples are certain non-polar amino acids, such as alanine, basic amino acids, such as histidine, and/or uncharged polar amino acids, such as glycine.

Antioxidants can be used to enhance the stability of the emulsion. Examples of some suitable lipophilic antioxidants include α-tocopherol, butylated hydroxytoluene (BHT), and L-ascorbic acid 6-palmitate. When employed, such are used in amounts of about 0.002 to about 0.2 gms/100 ml, preferably about 0.01 to about 0.10 grams/100 ml, an example of which is about 0.02 grams/100 ml.

The emulsions of the present invention can be administered by those techniques known in the art including orally and parenterally such as intravenously, intramuscularly and subcutaneously. When administered or introduced into the blood vessels, the particles in the emulsion are less than about 5 microns and most preferably about 0.5 micron or below.

The emulsions of the present invention satisfy the need for a stable, pharmacologically-suitable, lipid-based delivery system while at the same time meeting the specific requirements for retaining drug efficacy in vivo. The vehicle composition employed in the present invention is suitable for injection since, among other things, it avoids pharmaceutically undesirable organic solvents, solubilizers, oils, or emulsifiers.

The emulsions of the present invention are capable being terminally heat sterilized under standard conditions in a steam autoclave. These emulsions retain adequate physical and chemical stability during storage at 4°–8° C. for at least 18 months.

The sphingolipids employed actually serve as their own co-surfactants, stabilizing the emulsions. In fact, vehicle controls made in exactly the same fashion but without the sphingolipid drug are poor in quality and highly unstable. Attempts to terminally heat sterilize vehicle controls resulted in emulsion breakage, i.e., formation of large quantities of non-emulsified surface oil.

It was quite surprising that the emulsions of the present invention can be safely administered intravenously since such are positively charged acidic emulsions. It is commonly believed that cationic emulsion droplets will tend to bind to cell membranes and activate blood platelets, resulting in intravenous coagulation and thrombosis.

The vehicle composition employed in the present invention is chemically inert with respect to the incorporated sphingolipid. It delivers the selected sphingolipid in a concentration sufficient to permit a clinically acceptable infusion volume. In addition, the vehicle employed prevents loss of sphingolipid during administration, e.g. due to absorption onto plastic infusion sets, and minimizes acute toxicity of the surface active sphingolipid (e.g. hemolytic activity) compared to a solvent formulation.

It has been noted that the formulation remains stable without flocculation or coalescence upon dilution in vitro in 5% dextrose or upon mixing with human blood. Pharmacokinetics and tissue distribution for the sphingolipid in the vehicle used in the present invention are consistent with requirements for efficacy (e.g. minimum macrophage uptake).

Sphingolipids employed in the compositions of the present invention such as L-threo-dihydrosphingosine, also known as (2S,3S)-2-amino-1,3-octadecanediol or safingol, are potent inhibitors of protein kinase C, both in vitro and in vivo. Such are useful to enhance the efficacy of selected chemotherapeutic agents such as doxorubicin and cisplatin in the treatment of certain drug-resistant cancers. The present invention may also be used to deliver other pharmaceutically active sphingolipids intended, for example, as therapy for certain inflammatory conditions.

The presently recommended dose of safingol, administered in the formulation described by the present invention, is 120 mg per square meter body surface or about 200 mg for a typical adult patient. A sterile emulsion is first diluted to a convenient drug concentration (typically about 0.5 mg/ml) using 5% dextrose for injection. A standard chemotherapeutic agent, such as cisplatin or doxorubicin, is co-infused with safingol over approximately a one hour time period. This therapy may be safety repeated every 14 to 21 days. The safingol shows no acute toxicity when administered as described above, using the present invention. In contrast, when animals receive similar doses of safingol or other sphingolipids, whether administered in organic solvents or in aqueous vehicles, unacceptable acute toxicity is observed. Such toxicity may include intravascular hemolysis and lung embolism.

The following non-limiting examples are presented to further illustrate the present invention.

EXAMPLE 1

A water-in-oil emulsion containing about 20% by weight soybean oil, about 5 mg/ml safingol, about 0.3% by weight cholesterol, about 1% by weight Pluronic F68 (BASF Corp.), and about 0.02% α-tocopherol and HCl for pH adjustment to about 4 was prepared by adding the oil phase at temperatures of about 40°–60° C. to the aqueous phase at a temperature of about 40°–60° C. while processing with a high shear mixer (Ultra-Turrax T25; Tekmar Co., Cincinnati, Ohio) to form a uniform "premix" or "preemulsion."

The oil phase comprises the soybean oil, safingol, cholesterol, and α-tocopherol. The aqueous phase comprises the glycerin, Pluronic F68, α-tocopherol, hydrochloric acid for pH adjustment, and water. The above described premix is transferred to a high-pressure bench-top homogenizer (APV Rannie, Inc., St. Paul, Minn.; Model MINI-LAB 8.30H) for emulsification at 8000–10,000 psi at 40°–60° C. The product is filtered (Gelman Acro 50A, 5 μm) into borosilicate vials and then sterilized in a pressurized steam autoclave.

Physical and chemical characterization of the sterilized emulsion is performed as follows:

appearance: visual examination and phase-contrast microscopy pH: Standard hydrogen ion electrode drop size distribution: laser light scattering with Malvern MasterSizer Zeta potential: electrophoretic mobility with Malvern Zetasizer 2c, measured at pH 4.0 in 5 mM acetate buffer safingol concentration: HPLC analysis using a reverse phase system with a C18 column (ODS Hypersil), a methanol: water (9:1) mobil phase, and an evaporative, light scattering mass detector (Varex Corporation). Pharmacological activity of safingol may be tested using a mouse model involving phorbel ester-induced ear inflammation. Results are reported as 50% of the maximally effective anti-inflammatory dose ($ED_{50}$) in mg/kg body weight.

The emulsified droplets in this preparation have a volume-weighted mean diameter of 0.42 μm, with 90% of particles less than 0.66 μm. The Zeta potential is +55 mV. The amount of safingol recovered is 92% w/v and the biological efficacy ($ED_{50}$) thereof is 15 mg/kg.

EXAMPLE 2

Example 1 was repeated except that the oil was a mixture of 13% soybean oil and 7% oleic acid ethyl ester and the amount of, α-tocopherol was 0.1%. After sterilization, the pH of the emulsion is 5.51. The particles in the emulsion have a mean diameter of 0.29 μm and size (90th percentile) of 0.60 μm. The Zeta potential is +55mV. The amount of safingol recovered is 94% w/v and the $ED_{50}$ is 22 mg/kg.

What is claimed is:

1. An emulsion for administering a cationic sphingolipid to a patient in need thereof consisting of a pharmacologically acceptable lipoid as a hydrophobic phase dispersed in a hydrophilic phase, an effective amount of said sphingolipid, non-ionic surfactant and cholesterol in an amount sufficient to stabilize said emulsion and optionally at least one member selected from the group consisting of isotonic agent, antioxidant, nutritive agent, trace element and vitamin, and wherein said emulsion has a pH of about 2 to about 6.

2. The emulsion of claim 1 wherein said sphingolipid is L-threo-dihydrosphingosine or safingol.

3. The emulsion of claim 1 wherein said lipoid is selected from the group consisting of soybean oil, safflower oil, marine oil, sunflower seed oil, corn oil, black currant seed oil, borage oil, palm kernel oil, cotton seed oil, olive oil, medium chain triglycerides from coconut oil distillates, and mixtures thereof.

4. The emulsion of claim 1 wherein said lipoid is soybean oil.

5. The emulsion of claim 1 wherein the particles have a hydrodynamic mean diameter of less than 5 microns.

6. The emulsion of claim 1 wherein said mean diameter is 0.5 μm or less.

7. The emulsion of claim 1 wherein the amount of said sphingolipid is about 0.1 to about 1 g/100 ml, the amount of said lipoid is about 5 to about 30 g/100 ml, and the amount of said cholesterol is about 0.1 to about 1 g/100 ml.

8. The emulsion of claim 1 wherein the amount of said nonionic surfactant is about 0.1 to about 5 g/100 ml.

9. The emulsion of claim 8 wherein said nonionic surfactant is a block copolymer of polyoxyethylene and polyoxypropylene.

10. The emulsion of claim 1 wherein said block copolymer is poloxamer 188.

11. The emulsion of claim 1 which further includes an isotonic agent.

12. The emulsion of claim 11 wherein said isotonic agent is present in an amount of about 1 to about 3 g/100 ml.

13. The emulsion of claim 11 wherein said isotonic agent is glycerin.

14. The emulsion of claim 1 which further includes an antioxidant.

15. The emulsion of claim 14 wherein the antioxidant is present in an amount of about 0.002 to about 0.2 g/100 ml.

16. The emulsion of claim 1 wherein said antioxidant is α-tocopherol.

17. The emulsion of claim 1 being free of phospholipids of animal and vegetable origin.

* * * * *